United States Patent
O'Hara et al.

(10) Patent No.: US 11,547,396 B2
(45) Date of Patent: Jan. 10, 2023

(54) DEVICES AND METHODS FOR SECURING MEDICAL DEVICES WITHIN AN ANATOMY

(71) Applicant: W. L. Gore & Associates, Inc., Newark, DE (US)

(72) Inventors: Michael L. O'Hara, Baltimore, MD (US); Sherif A. Eskaros, Elkton, MD (US); Clifford P. Warner, West Chester, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 945 days.

(21) Appl. No.: 13/961,461

(22) Filed: Aug. 7, 2013

(65) Prior Publication Data

US 2014/0046366 A1 Feb. 13, 2014

Related U.S. Application Data

(60) Provisional application No. 61/681,688, filed on Aug. 10, 2012.

(51) Int. Cl.
*A61B 17/04* (2006.01)
*A61B 17/06* (2006.01)
(Continued)

(52) U.S. Cl.
CPC ........ *A61B 17/0401* (2013.01); *A61B 17/064* (2013.01); *A61B 17/068* (2013.01);
(Continued)

(58) Field of Classification Search
CPC .......... A61B 17/0401; A61B 17/06166; A61B 17/06066; A61B 2017/00668; A61B 2017/0409; A61B 2017/0412; A61B 2017/0427; A61B 2017/0464; A61B 2017/06171; A61B 2017/06176;
(Continued)

(56) References Cited

U.S. PATENT DOCUMENTS 4,485,816 A 12/1984 Krumme
5,002,563 A 3/1991 Pyka
(Continued)

FOREIGN PATENT DOCUMENTS

CN 102458313 A 5/2012
EP 1 749 484 2/2007
(Continued)

OTHER PUBLICATIONS

International Search Report, PCT-US2013/054052, Written Opinion, 14 pages, dated Nov. 14, 2013.
(Continued)

*Primary Examiner* — Todd J Scherbel (57) ABSTRACT

The present disclosure includes a plurality of securing devices. For example, the present disclosure includes securing devices comprising sutures, everting anchors, and inverting anchors. The sutures and anchors disclosed herein may be capable of deployment to a depth within a body lumen, such that body tissue external to the body lumen is not damaged by the devices. Moreover, in various embodiments, the securing devices described herein may couple one or more medical devices (e.g., stents, grafts, and/or stent-grafts) to body tissue such as a body lumen.

22 Claims, 9 Drawing Sheets

(51) Int. Cl.
  *A61B 17/064* (2006.01)
  *A61B 17/068* (2006.01)
  *A61B 17/00* (2006.01)
  *A61B 17/22* (2006.01)

(52) U.S. Cl.
  CPC .... *A61B 17/0644* (2013.01); *A61B 17/06166* (2013.01); *A61B 2017/00557* (2013.01); *A61B 2017/00867* (2013.01); *A61B 2017/0641* (2013.01); *A61B 2017/0645* (2013.01); *A61B 2017/0647* (2013.01); *A61B 2017/06176* (2013.01); *A61B 2017/22069* (2013.01)

(58) Field of Classification Search
  CPC .. A61B 2017/0618; A61B 2017/06076; A61B 2017/0645; A61B 2017/0647; A61B 2017/0649
  See application file for complete search history.

(56) References Cited

U.S. PATENT DOCUMENTS

| | | | |
|---|---|---|---|
| 5,478,354 | A | 12/1995 | Tovey et al. |
| 5,893,856 | A | 4/1999 | Jacob et al. |
| 5,972,024 | A * | 10/1999 | Northrup, III ... A61B 17/06166 606/151 |
| 7,918,873 | B2 | 4/2011 | Cummins |
| 8,202,311 | B2 | 6/2012 | Demetriades et al. |
| 2003/0074023 | A1 | 4/2003 | Kaplan et al. |
| 2004/0068276 | A1* | 4/2004 | Golden .............. A61B 17/0644 606/153 |
| 2004/0117004 | A1 | 6/2004 | Osborne et al. |
| 2004/0199188 | A1 | 10/2004 | Hanson et al. |
| 2005/0070924 | A1 | 3/2005 | Schaller et al. |
| 2005/0080454 | A1 | 4/2005 | Drews et al. |
| 2006/0253143 | A1 | 11/2006 | Edoga et al. |
| 2007/0112423 | A1 | 5/2007 | Chu |
| 2008/0045982 | A1 | 2/2008 | To et al. |
| 2008/0228030 | A1 | 9/2008 | Godin |
| 2008/0287989 | A1 | 11/2008 | Weisel |
| 2009/0240340 | A1 | 9/2009 | Levine et al. |
| 2009/0306681 | A1* | 12/2009 | Del Nido ........... A61B 17/0401 606/139 |
| 2010/0114119 | A1 | 5/2010 | McLawhorn et al. |
| 2010/0121359 | A1* | 5/2010 | Atui ..................... A61B 17/122 606/158 |
| 2010/0234886 | A1 | 9/2010 | Godin |
| 2010/0268029 | A1 | 10/2010 | Phan et al. |
| 2011/0087277 | A1 | 4/2011 | Viola et al. |
| 2011/0093002 | A1 | 4/2011 | Rucker et al. |
| 2012/0083808 | A1 | 4/2012 | Shriver |
| 2012/0245603 | A1 | 9/2012 | Voss |
| 2013/0133240 | A1* | 5/2013 | Beitzel .................. A01K 91/03 43/43.16 |
| 2014/0107674 | A1* | 4/2014 | Fujisaki ............. A61B 17/0469 606/148 |
| 2017/0333029 | A1 | 11/2017 | O'Hara et al. |
| 2018/0110635 | A1 | 4/2018 | Shaw |

FOREIGN PATENT DOCUMENTS

| | | |
|---|---|---|
| GB | 2 359 024 | 8/2001 |
| JP | 2005525837 | 7/2003 |
| JP | 2004-535897 | 12/2004 |
| JP | 2007-533362 | 11/2007 |
| WO | WO01/41624 | 6/2001 |
| WO | WO01/91628 | 12/2001 |
| WO | WO02/45593 | 6/2002 |
| WO | WO2004/060169 | 7/2004 |
| WO | WO2007/025019 | 3/2007 |
| WO | 2007/089843 A2 | 8/2007 |
| WO | 2008/108936 A1 | 9/2008 |
| WO | WO2009/132284 | 10/2009 |
| WO | WO2012/031204 | 3/2012 |
| WO | WO2012/058582 | 5/2012 |

OTHER PUBLICATIONS

Extended European Search Report dated Jun. 22, 2016—Application No. 13828143.1.
European Search Opinion Received for EP Application No. 13828143.1, dated Jun. 22, 2016, 7 pages.
European Search Report and Search Opinion Received for EP Application No. 19157322.9, dated Oct. 9, 2019, 9 pages.
International Preliminary Reporton Patentability received for PCT Patent Application No. PCT/US2013/054052, dated Feb. 19, 2015, 9 pages.

* cited by examiner

DEVICES AND METHODS FOR SECURING MEDICAL DEVICES WITHIN AN ANATOMY

CROSS REFERENCE

This application claims priority to U.S. Ser. No. 61/681,688 filed Aug. 10, 2012.

BACKGROUND

Field

The present disclosure generally relates to the field of medicine, and more particularly to securing devices, such as sutures and anchors, for securing medical devices within an anatomy or body (e.g., a human body).

Discussion of the Related Art

A variety of medical devices have been developed for implantation within an anatomy or body (e.g., a human body). Many such devices are implantable within a body lumen (e.g., the vasculature and/or gastrointestinal tract ("GI tract") of a human body). For instance, devices like stents, grafts, and stent-grafts may be implanted within the vasculature and/or GI tract of a human body to reinforce, replace, and/or bridge a damaged, unhealthy, or otherwise diseased portion of a body lumen. These devices may thus, in certain instances, guide blood and/or other material through a lumen defined by a cylindrical interior surface. During implantation, however, it is often necessary to anchor such devices in place, so that they will not migrate away from a damaged or diseased portion of the anatomy they are intended to repair.

Although techniques have been developed to hold devices like those described above in place, these techniques may suffer from a variety of shortcomings. For instance, a securing device (such as a medical suture, anchor, staple, or barb) may entirely penetrate a body lumen, such that a sharpened portion of the securing device is exposed to (and may damage) surrounding tissue. Similarly, a securing device may be deployed too tightly against a lumen wall, which may cause the securing device to migrate, over time, through the lumen wall. This may eventually free an implanted medical device from its proper location within a lumen. In addition, a securing device may be deployed such that it cannot be (easily) removed from a body lumen. For instance, although removal of a securing device may benefit an adequately healed patient and/or become necessary to relocate an improperly situated medical device, removal may yet be difficult, if not ill advised.

More suitable techniques for securing a medical device to an intended location are therefore desirable. For instance, a securing device capable of removal and/or relocation is desirable, particularly where a patient may not require permanent implantation of a medical device and/or the medical device is situated incorrectly. Similarly, a securing device capable of partial implantation in a vessel wall (e.g., such that surrounding tissue is not exposed to a sharpened or pointed portion of the device) is desirable. Likewise, a securing device resistant to migration is also beneficial and desirable.

SUMMARY

The present disclosure includes a securing device comprising a medical suture. In various embodiments, a suture may comprise a length of shape memory wire having a proximal stop tab, a body portion, and/or a sharp distal end. A suture may further curve or develop a curvature during deployment such that the suture may couple or stitch, for example, a medical device to a body lumen. The suture may only partially penetrate a body lumen. A suture may be stabilized during deployment and/or pressed against tissue to be sutured by a stabilizing device.

Further, in various embodiments, the present disclosure includes a securing device comprising an everting anchor. Such an anchor may evert during deployment to form a first anchor arm having a first arc ending in a first pointed or sharpened tip. An anchor may further evert during deployment to form a second anchor arm having a second arc ending in a second pointed or sharpened tip. An everting anchor may resemble a "seagull" in shape, and in a deployed configuration, the anchor may only partially penetrate a body lumen.

Further still, in various embodiments, the present disclosure includes a securing device comprising an inverting anchor. An inverting anchor may comprise a plurality of tines depending from a central portion. Each tine may invert during deployment to grasp a lumen wall. A profile defined by the endpoints of each of the plurality of tines may be substantially elliptical.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying figures referred to herein are not all drawn to scale, but may be exaggerated to illustrate various aspects of the present disclosure, and in that regard, the figures should not be construed as limiting. Finally, although the present disclosure may be described in connection with various principles and beliefs, the present disclosure should not be bound by theory.

Throughout this specification and in the claims, the term "distal" may refer to a location that is, or a portion of an intraluminal device (such as a delivery device and/or a medical device) that when implanted is, further downstream with respect to blood or fluid flow than another portion of the device. Similarly, the term "distally" may refer to the direction of blood or fluid flow or further downstream in the direction of blood or fluid flow.

The term "proximal" may refer to a location that is, or a portion of an intraluminal device (such as a delivery device and/or a medical device) that when implanted is, further upstream with respect to blood or fluid flow. Similarly, the term "proximally" may refer to the direction opposite to the direction of blood or fluid flow or upstream from the direction of blood or fluid flow.

With further regard to the terms proximal and distal, this disclosure should not be narrowly construed with respect to these terms. Rather, the devices and methods described herein may be altered and/or adjusted relative to the anatomy of a patient.

As used herein, the phrase "securing device" may refer to a device capable of securing a medical device within a body, as described herein. For example, in various embodiments, a securing device may comprise a suture, an anchor, a staple, a clip, a hook, a tack, a barb, and the like.

Likewise, as used herein, the phrase "medical device" may refer to a device capable of being secured within a body, as described herein. For example, in various embodiments, a medical device may comprise a stent, a graft, a stent-graft, and the like.

While the specific embodiments are described in greater detail below, in general, the present disclosure will focus primarily upon devices and methods for securing a medical device within a body (e.g., a human body). For instance, in various embodiments, these devices and methods may be applied to treat diseases of the vasculature and/or GI tract, including any disease where a body lumen is implanted with a medical device.

In addition, although the devices and methods described herein may focus on application of a medical device to a human body, these devices and methods may be more broadly applied to secure medical devices within any part of any body (human, mammalian, or otherwise). Moreover, although the disclosure provided herein may focus, in part, upon embodiments in which a medical device is secured to a body lumen, the devices and methods described herein may apply equally to tissue to tissue fixation as well as to fixation of medical devices to non-luminal body tissue.

In various embodiments, a securing device comprising a medical suture is disclosed. A suture may comprise a length of shape memory wire having a proximal stop tab, a body portion, and/or a sharp distal end. A suture may further curve or develop a curvature during deployment such that the suture may couple a medical device to a body lumen. Further, in various embodiments, a suture may be constructed with a particular radius of curvature, such that the suture only partially penetrates a body lumen (i.e., such that the suture is unable to penetrate an outer or exterior surface of a body lumen, thereby protecting surrounding tissue from damage by the suture). Further still, a suture may be stabilized during deployment and/or pressed against tissue to be sutured by a stabilizing device.

Additionally, in various embodiments, a securing device may comprise an everting anchor. Such an anchor may evert during deployment to form a first anchor arm having a first arc ending in a first pointed or sharpened tip. Such an anchor may further evert during deployment to form a second anchor arm having a second arc ending in a second pointed or sharpened tip. Further, in a deployed configuration, an anchor of this type may resemble a "seagull" in shape. As discussed briefly above and in greater detail below, an everting anchor may only partially penetrate a body lumen. Thus, as described, surrounding or exterior body tissue may be protected from damage by a deployed anchor (i.e., because the anchor deploys to a depth within a body lumen but does not pierce an exterior surface of the lumen).

A securing device may further comprise, in various embodiments, an inverting anchor having a plurality of tines depending from a central portion. Each tine may invert during deployment to grasp a lumen wall. Each tine may partially penetrate a lumen wall, but tines may also simply grasp tissue. A profile defined by the endpoints of each of the plurality of tines may be substantially elliptical. A substantially elliptical profile may inhibit motion by a medical device coupled to the inverting anchor in a variety of directions.

Figure 1A:
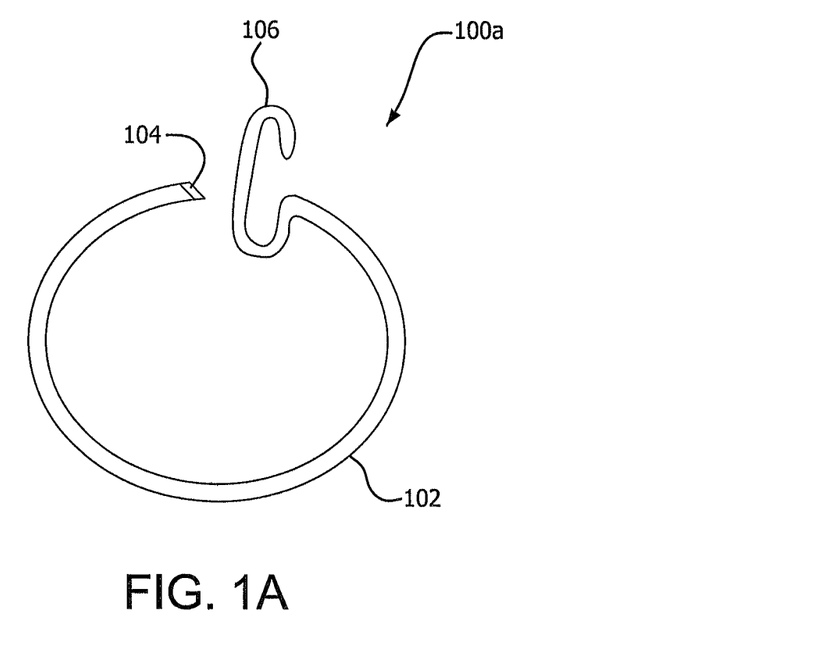
FIG. 1A illustrates a perspective view of a suture having a stop tab.
Figure 1B:
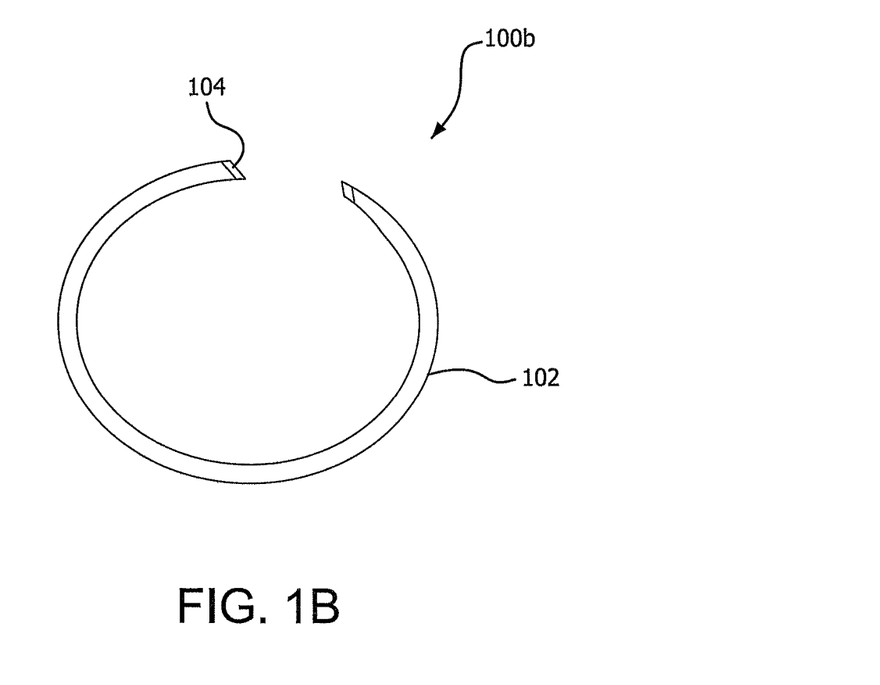
FIG. 1B illustrates a perspective view of a suture.

With reference now to FIGS. 1A and 1B, securing devices comprising sutures 100*a* and 100*b* (or "sutures" for ease of reference) are shown in their deployed configurations. In various embodiments, sutures may be formed from a length of shape memory wire (e.g., a length of Nickel Titanium, or NiTi, wire).

In various embodiments, sutures 100*a* and/or 100*b* may comprise a body portion 102, which may terminate in a sharpened or pointed (or, for simplicity, "sharp") distal tip 104. Sutures may, during deployment and as described herein, assume a curvature or curved shape such that sutures are capable of piercing a body lumen and/or a medical device.

Sutures (e.g., suture 100*a*) may further comprise, in various embodiments, a removal and/or stop tab 106. A stop tab 106 may comprise a variety of shapes, including, for example, any shape which is capable of being grasped for insertion and/or removal of a suture and/or any shape which is capable of limiting a depth of penetration of a suture within body tissue. For instance, a stop tab 106 may comprise an undulating shape, a shape having an apex portion coupled to a trough portion, a hook or hooked shape, a t-shape, an L-shape, and the like. In addition, in various embodiments, a stop tab 106 may comprise a proximal portion of body portion 102 and/or be coupled to a proximal portion of body portion 102. In some embodiments, sutures (e.g., suture 100*b*) may omit a stop tab 106. A stop tab 106 may, in some embodiments, be capable of being grasped by a mechanical retrieving tool, which may be inserted in a body lumen to retrieve and/or remove a suture by way of the stop tab 106. Further, in various embodiments, a suture may be retracted in situ (e.g., via a stop tab 106 and/or via any other suitable method) to remove or reposition a suture and/or medical device to be sutured. In addition, a stop tab 106 may further limit a depth of penetration (as described elsewhere herein) of a suture within a body lumen.

Thus, in various embodiments, a suture 100*a* may comprise a length of shape memory wire having a proximal stop tab 106, a body portion 102, and/or a sharp distal tip 104. Further, in various embodiments, a suture 100*b* may comprise a length of shape memory wire having a body portion 102 and/or a sharp distal tip 104.

In various embodiments, one or more sutures may be loaded into a delivery lumen in a straightened configuration and/or a substantially straightened configuration. In this regard, although sutures may assume a curvature or curved shape during deployment (as described herein), prior to deployment and to facilitate delivery to a body lumen, sutures may be inserted or loaded into a delivery lumen in a straightened and thus minimally biologically invasive configuration.

A delivery lumen may comprise, in various embodiments, any device and/or cannula shaped device capable of delivering a securing device such as a suture to a body lumen. Thus, a delivery lumen may comprise a hypotube (e.g., a metal hypotube), a working channel of an endoscope (e.g., a working channel of less than or equal to six millimeters), and the like. Similarly, in various embodiments, a delivery lumen may comprise an everting sleeve delivery system.

Figure 2:
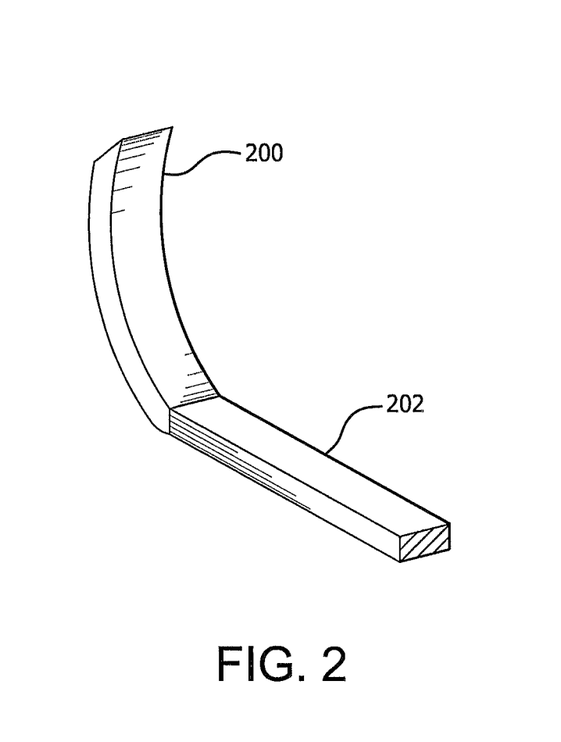
FIG. 2 illustrates a perspective view of a sharp suture deploying from a delivery lumen.

With reference now to FIG. 2, in various embodiments, sutures may comprise a shaped or formed wire. For instance, sutures may be edged and/or edgeless. An edgeless suture may comprise an elliptical and/or ovaloid wire and/or one or more rounded edges. An edged suture (e.g., edged suture 200) may, on the other hand, comprise a squared and/or rectangular wire and/or one or more edges having an angle (e.g., a ninety degree angle).

An edged suture may not, in various embodiments, rotate axially during deployment. For example, an edged suture may exit an edged or edgeless delivery lumen such that the suture is prevented, by its shape and/or the shape of the delivery lumen, from rotating, or twisting axially as it is deployed within a body lumen. In other words, a suture may be prevented, by its shape, from rotating as it exits a delivery lumen (e.g., an edged delivery lumen 202). Prevention of axial rotation during deployment may, in various embodiments, comprise an important advantage in that it may be important to ensure that a suture does not swivel or twist during deployment to pierce a body lumen (as described below) at an awkward or incorrect angle.

Figure 3:
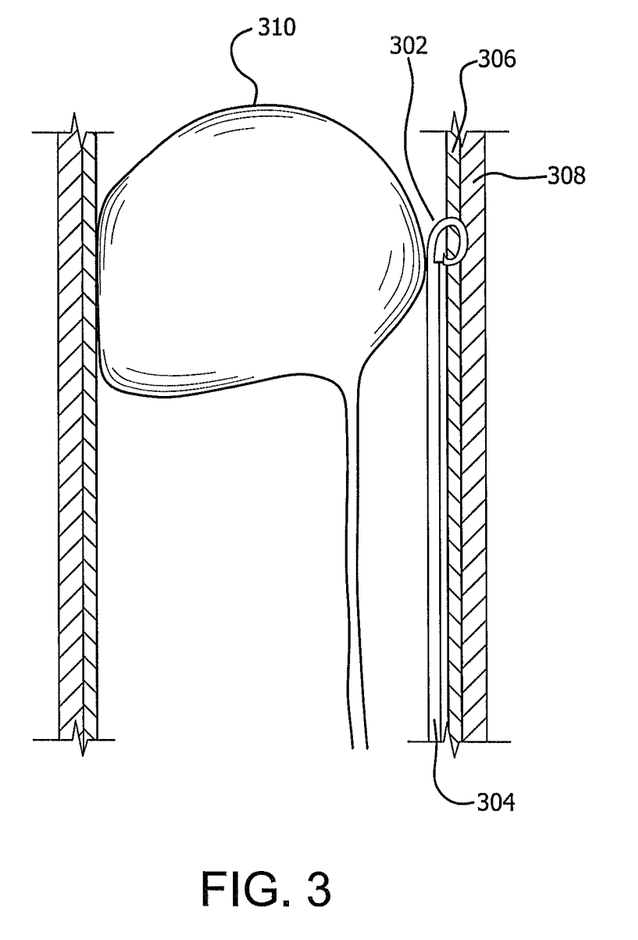
FIG. 3 illustrates a cross-sectional view of a suture deployed within a body lumen in which the suture is aided by an expandable stabilizing device.

With attention to FIG. 3, as shown, a suture 302 may be deployed within a body lumen. In various embodiments, a suture may be deployed together with a medical device (e.g., a stent or stent-graft) delivery system. More particularly, a suture 302 may be deployed within a body lumen such that a sharp distal tip of suture 302 exits a distal end of a delivery lumen 304. As the suture 302 exits the delivery lumen 304, the suture 302 may begin to assume or develop a curved shape. The suture 302 may assume this shape, as described above, because the suture 302 may be constructed from a shape memory alloy (e.g., NiTi), which may have elastic and/or superelastic properties. Thus, as the suture 302 exits the delivery lumen 304, a sharp distal tip of the suture 302 may pierce a lumen wall of a medical device 306 (e.g., a stent or stent-graft). The suture 302 may continue to exit the delivery lumen 304, whereby, as the suture 302 continues to assume a curved shape, the suture 302 may pass through the medical device 306 and into a body lumen wall 308 (e.g., a blood vessel wall). The suture 302 may, as shown, continue to deploy within the body lumen wall 308, so that the suture 302 loops back toward the axis of the delivery lumen 304 until the suture 302 is fully deployed in a ring-like or annular configuration.

In various embodiments, a fully deployed suture 302 may only partially penetrate a body lumen wall 308. For example, a fully deployed suture 302 may pierce an inner surface, but not an outer surface, of a body lumen wall 308. In other words, a suture 302 may be deployed within a body lumen such that no portion of the suture 302 exits an outer or exterior surface of a body lumen wall 308. However, in certain embodiments, a suture may be deployed so that at least a portion of the suture exits an exterior surface of a body lumen wall 308.

Further, in various embodiments, a sharp distal tip of a suture may remain embedded within the body lumen such that it is not exposed outside of the lumen. Additionally, in various embodiments, a sharp distal tip (although it may not penetrate an outer surface of a body lumen wall 308) may nevertheless re-pierce an inner surface of the body lumen wall 308 as it loops back toward the axis of the delivery lumen 304, so that the tip is exposed, in certain embodiments, within the body lumen. A suture 302 may thus act to couple a medical device 306 to a body lumen wall 308, yet obviate a risk that the suture may damage tissue outside of the lumen wall 308.

To accomplish these features, a suture 302 may be constructed to a particular length and/or such that it is limited during deployment by a particular radius of curvature. In this manner, a suture 302 may be constructed to penetrate a body lumen wall 308 to a specific depth and/or such that the suture 302 completely pierces a body lumen wall, as described above.

With further regard to suture deployment, in various embodiments, a stabilizing device 310 may be deployed within a body lumen to aid deployment of a suture 302. A stabilizing device 310 may comprise any device which may be used to stabilize a suture 302 during deployment. For example, in various embodiments, a stabilizing device 310 may comprise a medical balloon, such as an inflatable medical balloon and/or an expandable basket, such as an expandable wire basket.

A stabilizing device 310 may be delivered, as described above, together with and/or as part of a medical device delivery system. A stabilizing device 310 may be deployed so that the device 310 presses against the delivery lumen 304 as a suture 302 is deployed from the delivery lumen 304. Thus, the stabilizing device 310 may press or hold the delivery lumen 304 flush against a location on a body lumen wall 308 to be sutured. This may assure that the correct location is sutured. In addition, as the stabilizing device 310 may apply a pressure against the portion of the body lumen wall 308 to be sutured, the device 310 may facilitate penetration of a suture into the body lumen wall 308.

Figure 4:
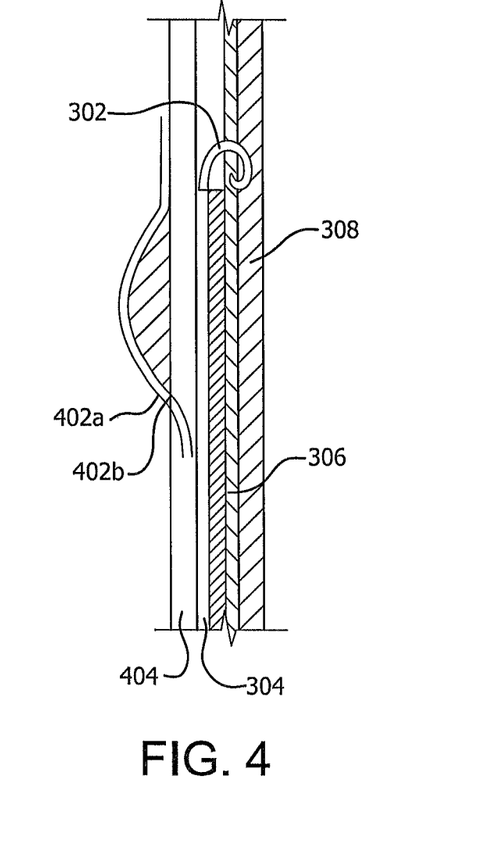
FIG. 4 illustrates a cross-sectional view of a suture deployed within a body lumen in which the suture is aided by a wire stabilizing device.

With reference to FIG. 4, a stabilizing device may, in various embodiments, comprise a delivery lumen 404 having one or more lines or wires, e.g., 402a and/or 402b, which may exit and reenter the delivery lumen 404 such that each wire 402a and 402b experiences an axially compressing force and so forms a bow or arc external to the delivery lumen 404. More particularly, each wire 402a and 402b may exit the lumen 404 at an exit location proximal to a suture location and reenter the lumen 404 at a reentry location that is substantially the location to be sutured. The axially compressing force (which may cause the wires to bunch into an arc between the exit location and the reentry location) may, in various embodiments, result from a difference between the length of each wire extended between the exit location and the reentry location and the length of the delivery lumen between each location. Specifically, the force may arise because the linear distance between the exit location and the reentry location is less than the length of each wire 402a and/or 402b extended between each location.

Thus, during deployment, a physician may manipulate a delivery lumen 404 such that the reentry location substantially overlaps with a site to be sutured. In this configuration, wires 402a and 402b may exert some pressure against the delivery lumen 404 at the reentry location and/or suture site. In addition, in various embodiments, each wire 402a and/or 402b may be deployed from within an isolated or unique delivery lumen, and these may, in various embodiments, comprise smaller diameter lumens within delivery lumen 404. Moreover, in various embodiments, a physician may apply a pressure against a proximal portion of wires 402a and/or 402b (e.g., at a location proximate to an exit location), such that the wires 402a and/or 402b are urged in a distal direction and, forming a non-uniform or skewed arc, apply a greater pressure proximate to the suture site. A physician may apply such pressure, for example, using a medical balloon and/or wire basket, as described above.

Figure 5A:
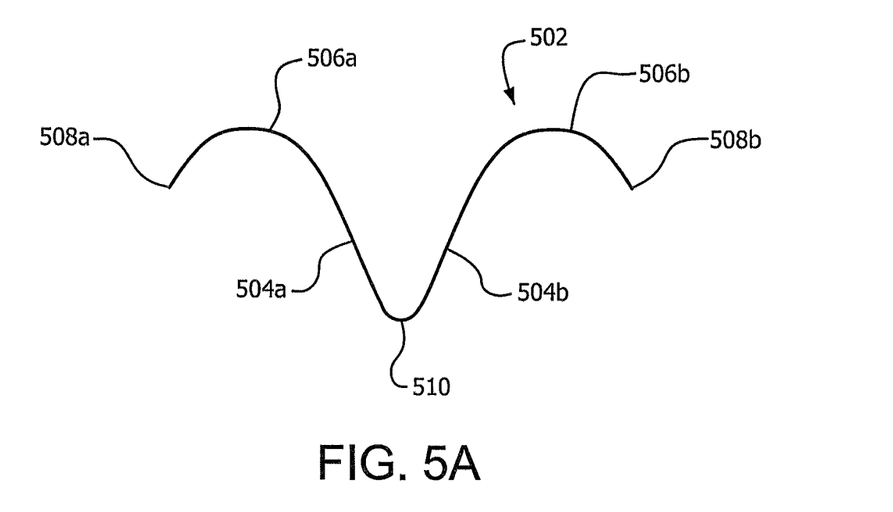
FIG. 5A illustrates a front view of an everting anchor.

Turning now to FIG. 5A, a securing device comprising an everting anchor 502 is shown. In various embodiments, an anchor 502 may comprise a length of shape memory wire (e.g., a NiTi wire, as described above). An anchor 502 may further evert during deployment to form a first anchor arm 504a having a first arc 506a ending in a first pointed or sharpened tip 508a. An anchor 502 may further evert during deployment to form a second anchor arm 504b having a second arc 506b ending in a second pointed or sharpened tip 508b. Moreover, each anchor arm 504a and 504b may be symmetrical to the other anchor arm about a centerline defined by a nadir, depression, or trough 510 between each anchor arm. Thus, in a deployed configuration, an anchor 502 may resemble a "seagull" in shape.

Figure 5B:
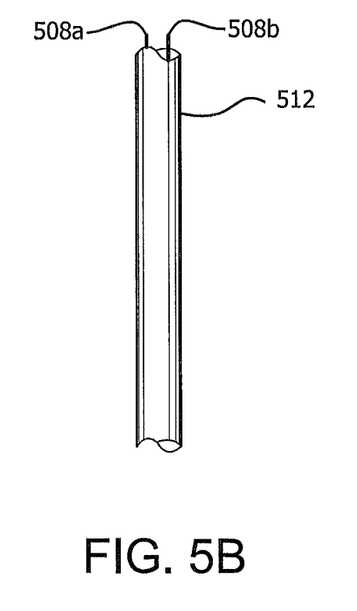
FIG. 5B illustrates a first front view of an everting anchor deploying from a delivery lumen.
Figure 5C:
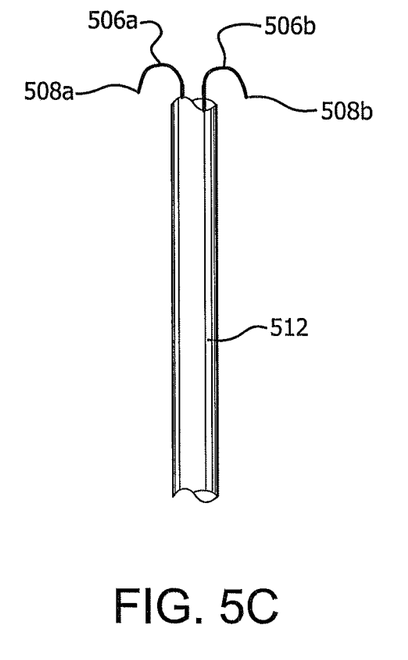
FIG. 5C illustrates a second front view of an everting anchor deploying from a lumen.
Figure 5D:
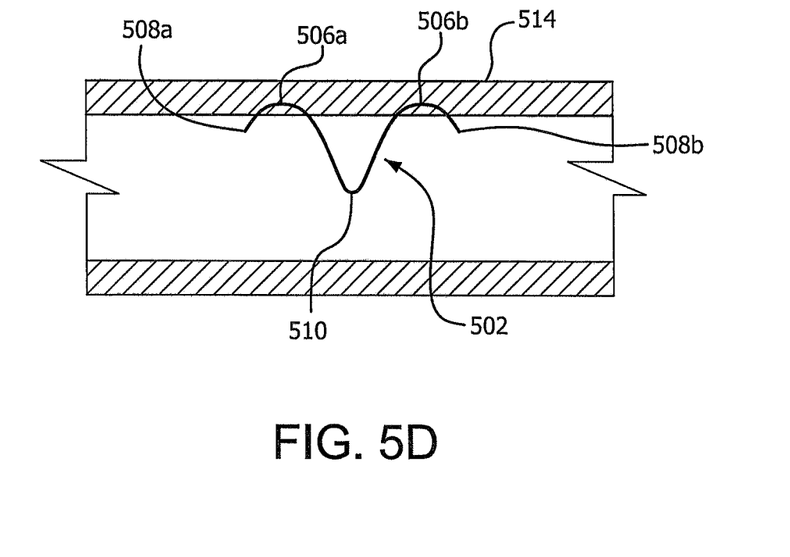
FIG. 5D illustrates a cross-sectional view of an everting anchor deployed within a body lumen.

With respect to deployment and referring to FIGS. 5B-5D, an anchor 502 may be compressed for delivery within a delivery lumen. For example, an anchor 502 may be compressed within a delivery lumen 512 such that a first anchor arm 504a and a second anchor arm 504b are disposed within the lumen 512 so that each arm is substantially parallel to the other arm (see, e.g., FIG. 5B). The pointed tip 508a and 508b of each anchor arm 504a and 504b may project from the delivery lumen 512 such that each tip is able to pierce a body lumen wall. For instance, each pointed tip may project, during an early stage of deployment, from the delivery lumen 512 such that each tip may be placed (e.g., by a physician manipulating the delivery lumen 512) at an angle (e.g., a ninety degree angle) to a lumen wall. Thus, each tip may be positioned to best or most easily penetrate a lumen wall.

Further, in various embodiments, and with particular reference to FIGS. 5C and 5D, an anchor 502 may deploy such that each pointed tip 508a and 508b of the anchor 502 penetrates an inner surface of a lumen wall 514. An anchor 502 may be further deployed, in various embodiments, such that the anchor only partially penetrates a lumen wall. Thus, for example and as shown, an anchor 502 may be deployed so that, as the anchor everts from the delivery lumen 512, each arc 506a and 506b rises to a depth within a body lumen 514 but does not exit or pierce an outer surface or wall of the lumen 514. In various embodiments, however, one or both arcs 506a and 506b may rise out of the body lumen 514 and into surrounding tissue. Additionally, in various embodiments, each pointed tip 508a and 508b may re-penetrate the inner wall of the body lumen 514 during final deployment. However, in other embodiments, one or both of the pointed tips 508a and 508b may not re-penetrate the inner wall of the body lumen 514, but remain embedded within the body lumen 514. Thus, as the anchor 502 is deployed from the delivery lumen 512, each anchor arm 504a and 504b may evert to assume the deployed configuration as shown in FIG. 5A, and the anchor 502 may spring back into its original formed "seagull" shape within a body lumen.

In various embodiments, an anchor 502 may be especially useful for the purpose of anchoring medical devices (e.g., stents) within the GI tract. For instance, a plurality of anchors 502 may be fixed or deployed within the GI tract and one or more medical devices coupled to the plurality of anchors 502 to stabilize and anchor the one or more medical devices within the GI tract. In various embodiments, a medical device may be tied or coupled to an anchor 502, and/or an anchor 502 may be deployed from within a medical device (as described above) such that the anchor first penetrates the medical device and next penetrates a body lumen wall.

Figure 6A:
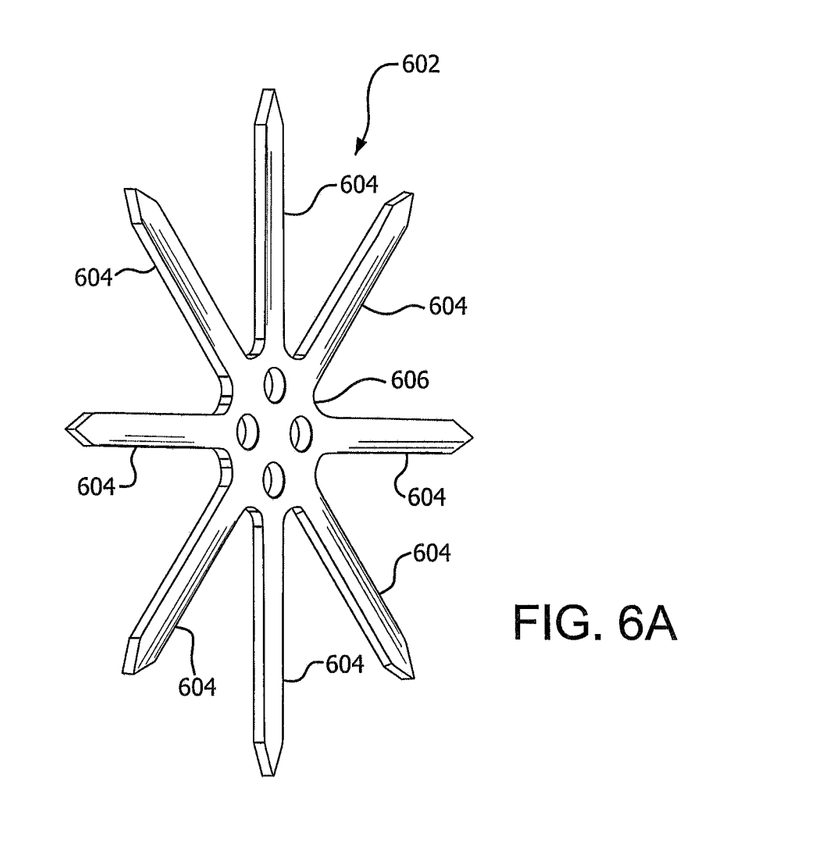
FIG. 6A illustrates a perspective view of an inverting anchor in an undeployed configuration.

Referring now to FIG. 6A, a securing device comprising an inverting anchor 602 is shown. An inverting anchor 602 may comprise a plurality of prongs or tines 604, each of which may depend from a central portion 606. In various embodiments, each tine 604 may terminate in a pointed or grasping tip, which may be useful for grasping, holding, and/or penetrating tissue within a body (e.g., a lumen wall). Further, in various embodiments, each tine 604 may be of approximately a same length. Further still, in various embodiments, a line drawn between each grasping tip may approximately define an ellipse, or in other words, a profile defined by an endpoint of each grasping tip may approximately define an ellipse.

Figure 6B:
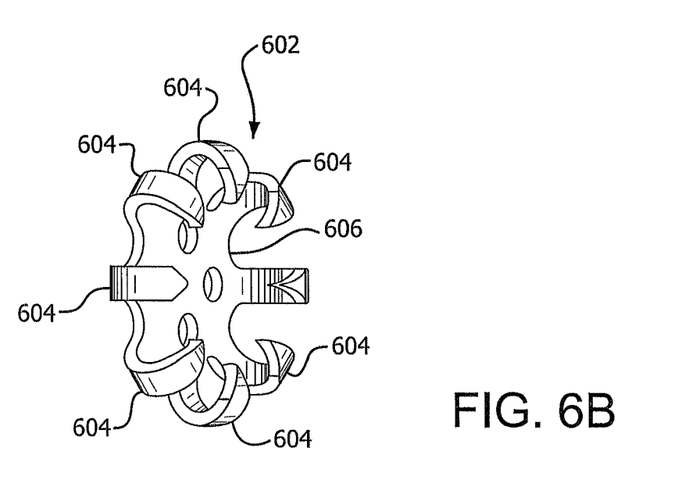
FIG. 6B illustrates a perspective view of an inverting anchor in a deployed configuration.

Each tine 604 of an anchor 602 may further comprise a shape memory material (e.g., NiTi, as described above), which may, in various embodiments and as shown by FIG. 6B, assume a curvature, in various embodiments, in response to entering an austenite phase (e.g., in response to being heated to a particular temperature, e.g., a typical normothermic human body temperature). In various embodiments, each tine 604 may further assume a curvature in response to removal of a delivery sheath, which may apply pressure sufficient to cause each tine to lay flat against an inner surface of a lumen defined by the delivery sheath.

Figure 7A:
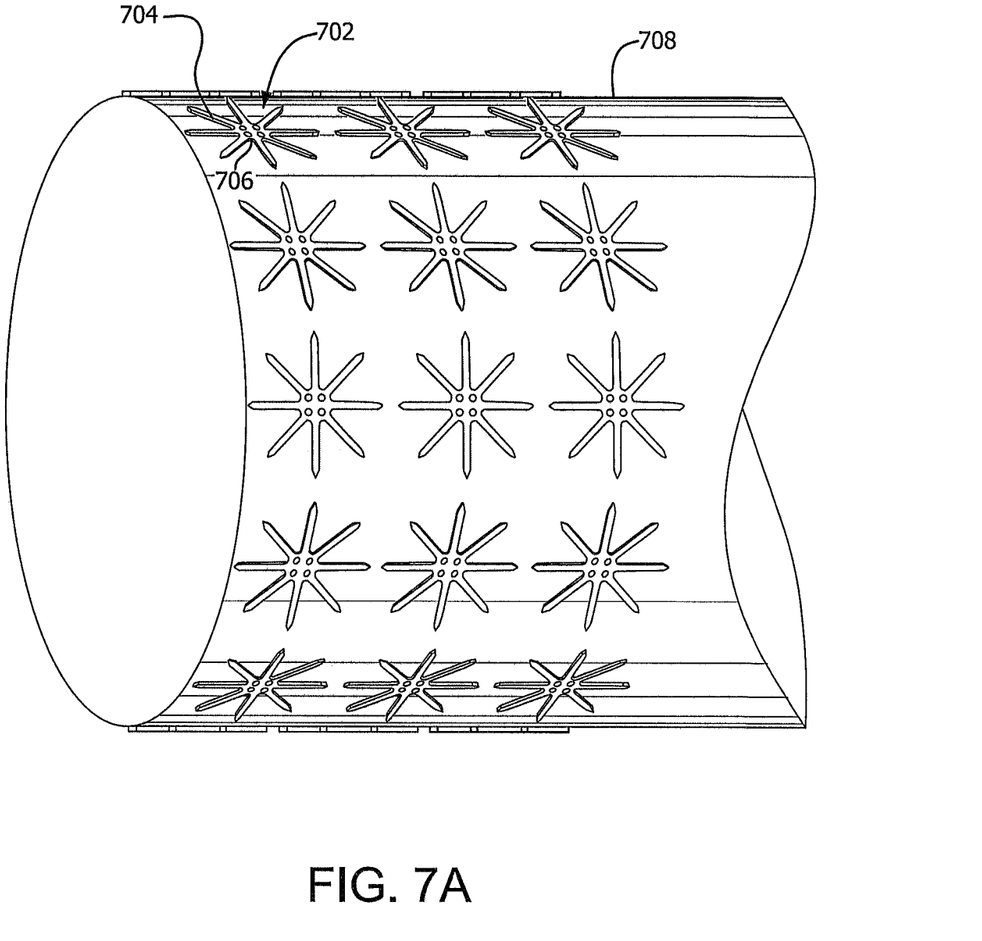
FIG. 7A illustrates a perspective view of a plurality of undeployed inverting anchors coupled to a medical device.

In various embodiments, and referring to FIG. 7A, one or more inverting anchors 702, consisting of a central portion 706 and tines 704, may be coupled to an outer surface of a medical device 708 (e.g., a stent or stent-graft). More particularly, in various embodiments, a plurality of anchors 702 may be distributed (e.g., substantially evenly) over the surface of a medical device 708 such that, for example, at least a portion of the medical device 708 is ringed or covered by substantially evenly spaced anchors 702. In addition, in various embodiments, a central portion 706 of one or more anchors 702 may be coupled to an outer surface of a medical device 708. A central portion 706 may be coupled or otherwise bonded to an outer surface of a medical device 708 by any coupling or bonding technique known in the art (e.g., chemical, thermal adhesion, metallurgical adhesion or bonding, integral construction with the medical device).

Figure 7B:
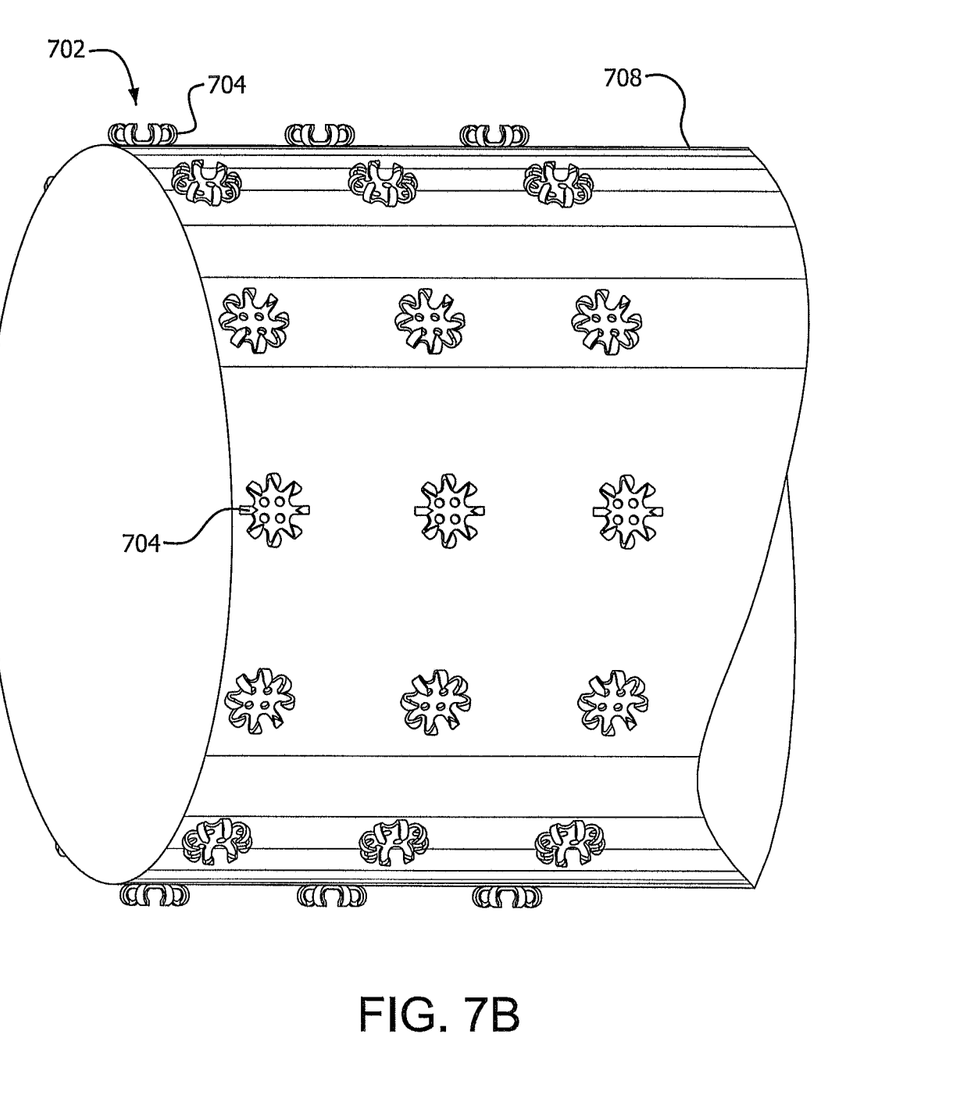
FIG. 7B illustrates a perspective view of a plurality of deployed inverting anchors coupled to a medical device.

Accordingly, with reference to FIG. 7B, each tine 704 may, during deployment, invert to assume a curvature or take on a curved shape. As discussed, the tines 704 of an anchor 702 may assume such a shape in order to grasp, hold, and/or pierce tissue. For example, where a medical device 708 is deployed within a body lumen (e.g., a blood vessel), each anchor 702 coupled to an outer surface of the medical device 708 may grasp and hold a body lumen wall. Thus, a medical device may be secured within a body lumen by a plurality of anchors 702, the tines 704 of which may invert during deployment to grasp and/or penetrate surrounding tissue. In various embodiments, a generally circular or elliptical anchor design (as described above) may limit a medical device from moving in any direction. Thus, a circular or elliptical anchor design may operate to secure a medical device against motion in all directions. Further, where tines 704 penetrate a body lumen wall, as described elsewhere herein, the tines 704 may only partially penetrate the body lumen wall (i.e., an exterior surface of the lumen wall may not be penetrated), and this may protect surrounding tissue from damage by the tines 704.

In various embodiments, a securing device may comprise a threaded or threadable structure. Similarly, in various embodiments, a delivery lumen may comprise a threaded or threadable structure. For example, where a securing device comprises a threaded structure, the device may rotate through a threaded delivery lumen and/or deploy within a body lumen and/or body tissue in a rotating manner. Simply put, in various embodiments, a securing device may be deployed like a screw. A securing device thus deployed may incise or cut a spiraling channel within body tissue, which may aid in the secure placement of the device within the tissue.

Similarly, in various embodiments, any of the securing devices described herein may include or incorporate one or more barbs or hooks. For example, a securing device may include one or more barbs, each of which may have a pointed tip that points in a distal direction. Thus, a barbed securing device may be easily deployed within tissue but resist motion in a distal direction).

Further, in various embodiments, a plurality of securing devices may be loaded into a delivery lumen for sequential delivery within a body. These devices may be loaded within a delivery lumen in a straightened configuration and/or a substantially straightened configuration, which may facilitate delivery to body tissue in a minimally biologically invasive manner.

With brief regard to grafts and stent-grafts, many graft materials are known, and in various embodiments, these materials can be used in combination and assembled together to comprise a graft. These materials may be further extruded, coated and/or formed from wrapped films, and/or a combination thereof. Polymeric materials, biodegradable materials, and/or natural materials can be used for specific applications.

In various embodiments, a graft may comprise synthetic polymers including nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends, and copolymers. In a variety of embodiments, a graft may be made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Further, in a variety of embodiments, a graft may comprise expanded fluorocarbon polymers (especially PTFE).

In various embodiments, fluoropolymers may include polytetrafluoroethylene (PTFE), expanded PTFE (ePTFE), fluorinated ethylene propylene (FEP), copolymers of tetrafluoroethylene (TFE) and perfluoro (propyl vinyl ether) (PEA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). In various embodiments, a graft may comprise any combination of the materials listed above. Further, in various embodiments, a graft may be substantially impermeable and/or permeable to bodily fluids. A substantially impermeable graft may be made from materials that are substantially impermeable to bodily fluids or can be constructed from permeable materials treated or manufactured to be substantially impermeable to bodily fluids (e.g. by layering different types of materials described above or known in the art). In various embodiments, a medical device, as described above, may be made from any combination of the materials described above, including ePTFE.

Any stent may be generally cylindrical when restrained and/or when unrestrained and may comprise helically arranged undulations having a plurality of helical turns. In a variety of embodiments, undulations may be aligned so that they are "in-phase" with each other. More specifically, undulations may comprise apices in opposing first and second directions. When these undulations are in-phase, apices in adjacent helical turns are aligned so that apices can be displaced into respective apices of a corresponding undulation in an adjacent helical turn. In certain embodiments, undulations may have a sinusoidal shape, a U shape, a V shape, and/or an ovaloid shape.

In various embodiments, a stent may be fabricated from a variety of biocompatible materials including commonly known materials (or combinations of materials) used in the manufacture of implantable medical devices. Such materials may include 316L stainless steel, cobalt-chromium-nickel-molybdenum-iron alloy ("cobalt-chromium"), other cobalt alloys such as L605, tantalum, nitinol, or other biocompatible metals. In some embodiments, any stent and/or stent-graft described herein may comprise a balloon expandable stent and/or stent-graft and/or a self-expanding stent and/or stent-graft. Further, in certain embodiments, a stent may comprise a wire wound stent, which may or may not comprise undulations.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A suture constructed from a length of shape memory wire comprising:
 a proximal stop tab at a proximal end of the suture and terminating in a singular distal sharp tip at a distal end of the suture, the suture assuming a curved shape during deployment such that the singular distal sharp tip is configured to pierce an inner surface of a body lumen wall of a body lumen and re-pierce the inner surface of the body lumen wall during deployment in a manner that protects surrounding body tissue from damage by the singular distal sharp tip,
 wherein the stop tab includes two hooked ends connected by a linear portion, the two hooked ends extending in the same direction away from the linear portion to define an opening between the two hooked ends, the stop tab has an open portion for receiving a retrieval device through the opening to facilitate removal of the suture from the body lumen wall of the body lumen and further configured to limit the depth of penetration of the suture,
wherein the suture is configured to only partially penetrate the body lumen wall in a deployed configuration, and
wherein the suture is configured for deployment from a delivery lumen positioned within the body lumen.

2. The suture of claim 1, wherein the suture is configured to be pressed against a location on the body lumen wall to be sutured by a basket.

3. The suture of claim 1, wherein the suture is configured to couple a medical device to the body lumen wall.

4. The suture of claim 1, wherein in said deployed configuration, said suture has an annular configuration.

5. The suture of claim 1, wherein the suture is configured to take on a curved shape such that suture extends from the proximal stop tab through an arcuate path with the sharp tip positioned adjacent the proximal stop tab.

6. A suture having a proximal end and a distal end, the suture comprising:
a stop tab at the proximal end of the suture and comprising two hooked ends connected by a linear portion, at least one of the two hooked ends, the two hooked ends extending away from the linear portion in the same direction to define an opening between the two hooked ends, the stop tab having an open portion for receiving a retrieval device through the opening to facilitate removal of the suture from the body lumen wall of the body lumen and further configured to limit the depth of penetration of the suture; and
a shape memory body portion coupled to the stop tab, wherein the shape memory body portion assumes a curved shape during deployment such that a singular distal sharp tip of the shape memory body portion at the distal end of the suture is configured to pierce an inner surface of a body lumen wall of a body lumen and re-pierce the inner surface of the body lumen wall in a manner such that an outer surface of the body lumen wall is not pierced and the suture is configured to only partially penetrate the body lumen wall in a deployed configuration,
wherein the suture is configured for deployment from a delivery lumen positioned within the body lumen.

7. The suture of claim 6, wherein the suture further comprises an edge that inhibits axial rotation of the suture during deployment.

8. The suture of claim 6, wherein in said deployed configuration, said suture has an annular configuration.

9. The suture of claim 6, wherein the suture is configured to take on a curved shape such that suture extends from the stop tab through an arcuate path with the sharp tip positioned adjacent the stop tab.

10. A securing device comprising:
a stent including a delivery lumen, the stent configured to be disposed in a body lumen defined by a body lumen wall having an inner surface and an outer surface,
a shape memory suture comprising a stop tab at a proximal end of the suture and configured for deployment from the delivery lumen and a singular sharp tip at a distal end of the suture, wherein the shape memory suture assumes a curved shape during deployment for suturing the body lumen wall to the stent,
wherein the stop tab comprises two hooked ends connected by a linear portion, the two hooked ends extending away from the linear portion in the same direction to define an opening between the two hooked ends, the stop tab having an open portion for receiving a retrieval device through the opening to facilitate removal of the suture from the body lumen wall of the body lumen and further configured to limit the depth of penetration of the suture,
wherein in a deployed configuration, the shape memory suture is configured to pierce the inner surface of the body lumen wall and re-pierce the inner surface of the body lumen wall and is configured to only partially penetrate the body lumen wall in the deployed configuration, and
wherein the suture is configured for deployment from the delivery lumen positioned within the body lumen.

11. The securing device of claim 10, wherein the securing device is capable of being pressed against tissue to be sutured by a plurality of wires partially disposed within a lumen.

12. The securing device of claim 10, wherein the securing device is capable of being repositioned in situ.

13. The securing device of claim 10, wherein the suture further comprises an edge that inhibits axial rotation of the suture during deployment.

14. The securing device of claim 10, wherein the outer surface of the body lumen wall is not pierced.

15. The securing device of claim 10, wherein in said deployed configuration, said suture has an annular configuration.

16. The securing device of claim 10, wherein the delivery lumen is held flush against a location on the body lumen wall during deployment of the suture.

17. The securing device of claim 16, further comprising a stabilizing device configured to press the delivery lumen against the location on the body lumen wall.

18. The securing device of claim 10, wherein the delivery lumen is substantially parallel to the inner surface of the body lumen wall.

19. The securing device of claim 10, wherein the suture is configured to take on a curved shape such that suture extends from the stop tab through an arcuate path with the sharp tip positioned adjacent the stop tab.

20. A suture constructed from a length of shape memory wire comprising:
a proximal stop tab and terminating in a singular distal sharp tip, the suture assuming a curved shape during deployment such that the singular distal sharp tip is configured to pierce an inner surface of a body lumen wall of a body lumen and re-pierce the inner surface of the body lumen wall during deployment, wherein the stop tab comprises two hooked ends connected by a linear portion, the two hooked ends extending away from the linear portion in the same direction to define an opening between the two hooked ends, at least one of the two hooked ends has having an open portion for receiving a retrieval device through the opening between the two hooked ends;
wherein the suture is configured to only partially penetrate the body lumen wall in a deployed configuration;
wherein the suture is configured for deployment from a delivery lumen positioned within the body lumen; and
wherein a cross-section of the suture forms a shape having one or more angled edges.

21. The suture of claim 20, wherein the suture includes a deployed configuration in which the suture is in an annular configuration.

22. The suture of claim 20, wherein the suture is configured to take on a curved shape such that suture extends from the stop tab through an arcuate path with the sharp tip positioned adjacent the stop tab.

* * * * *